United States Patent
Hunt et al.

(10) Patent No.: US 7,690,920 B2
(45) Date of Patent: Apr. 6, 2010

(54) HIGH STRENGTH SUBSTRUCTURE REINFORCEMENT FOR CROWNS AND BRIDGES

(76) Inventors: Peter R. Hunt, 514 Humboldt Plz., Manhattan, KS (US) 66502; Robert D. Sager, 514 Humbolodt Plz., Manhattan, KS (US) 66502

( * ) Notice: Subject to any disclaimer, the term of this patent is extended or adjusted under 35 U.S.C. 154(b) by 1163 days.

(21) Appl. No.: 11/107,519

(22) Filed: Apr. 15, 2005

(65) Prior Publication Data

US 2006/0234188 A1   Oct. 19, 2006

(51) Int. Cl.
*A61C 5/08* (2006.01)
(52) U.S. Cl. .................... 433/218; 433/223
(58) Field of Classification Search .......... 433/172, 433/173, 218, 213
See application file for complete search history.

(56) References Cited

U.S. PATENT DOCUMENTS

| | | | | |
|---|---|---|---|---|
| 3,328,879 | A * | 7/1967 | Bax | 433/218 |
| 3,487,544 | A * | 1/1970 | Weissman | 433/218 |
| 4,681,542 | A * | 7/1987 | Baum | 433/172 |
| 5,002,489 | A * | 3/1991 | Fischer et al. | 433/218 |
| 5,314,335 | A * | 5/1994 | Fung | 433/223 |
| 5,342,201 | A * | 8/1994 | Oden | 433/223 |
| 5,788,498 | A * | 8/1998 | Wohlwend | 433/223 |
| 5,810,590 | A * | 9/1998 | Fried et al. | 433/172 |
| 6,244,867 | B1 * | 6/2001 | Aravena et al. | 433/172 |
| 6,461,160 | B1 * | 10/2002 | Sutter | 433/173 |
| 6,672,871 | B2 * | 1/2004 | Hurson | 433/172 |
| 2002/0177106 | A1 * | 11/2002 | May et al. | 433/173 |
| 2003/0039943 | A1 * | 2/2003 | Worthington | 433/218 |
| 2003/0211445 | A1 * | 11/2003 | Klardie et al. | 433/173 |
| 2004/0101806 | A1 * | 5/2004 | Kumar et al. | 433/173 |
| 2006/0014120 | A1 * | 1/2006 | Sapian | 433/173 |

\* cited by examiner

*Primary Examiner*—Ralph A Lewis
(74) *Attorney, Agent, or Firm*—Sonnenschein Nath & Rosenthal LLP; Bryan P. Stanley

(57) ABSTRACT

A reinforcement for a dental restoration substructure is provided. The reinforcement is a generally annular structure that protrudes from the body of the substructure generally near an occlusal portion of the restoration. The annular structure provides a support for veneering porcelain at the location of the greatest thickness of the porcelain and at the location where occlusal stress is applied, and fractures of veneering porcelain are commonly experienced.

21 Claims, 1 Drawing Sheet

HIGH STRENGTH SUBSTRUCTURE REINFORCEMENT FOR CROWNS AND BRIDGES

FIELD OF THE INVENTION

The present invention relates generally to prosthodontic systems, methods and apparatuses. More particularly, the present invention is concerned with a high strength substructure for crowns and bridges and a process for manufacturing dental crowns and bridges having a high strength substructure.

BACKGROUND OF THE INVENTION

For some time, dental prostheses were produced from porcelain veneering material bonded onto a metal framework (substructure, or core). This porcelain-fused-to-metal ("ceramo metal") construction required a fairly bulbous metal core, with a fairly uniform porcelain thickness to avoid delamination under sheer conditions. More recently, dentists have been offered high strength ceramic materials as substitutes for the conventionally metal substructures in ceramo-metal crowns and/or bridges. These porcelain veneer fused to non-metal core crowns/bridges offer reduced labor costs, equivalent or superior precision to ceramo-metal alternatives, improved aesthetics, excellent bonds to the underlying high-strength ceramic sub-structure, reduction in thermal stresses, and reduced thermal conductivity.

Particular emphasis is placed on recent improvements in strength of the various new non-metal substructure materials. Traditional ceramic cores have compressive strengths in the region of 150-200 MPa. Alumina based cores claim strengths in the region of 400-600 MPa, and Zirconia cores have strengths ranging from 900-1200 MPa. Notwithstanding the impressive strengths of these substructure materials, these figures are deceptive due to the more limited strength of the veneering materials used for the crowns and/or bridges. Furthermore, the more aesthetic and much weaker veneering materials are not adequately supported by the higher strength ceramic core, often resulting in fracturing of the veneering porcelain while the ceramic core remains intact.

In restorations supported by implants instead of teeth, the fracture potential may be increased even more. This increased fracture potential is caused in part by an increase in the bulks of veneering porcelain. First, implants tend to be placed more lingually than the teeth they are replacing, which often results in more unsupported buccal porcelain. Second, the diameter of an implant platform is often smaller than the tooth it is replacing, giving rise to still bigger bulks of unsupported porcelain. The situation is further complicated by implants being more rigid than teeth, while at the same time resulting in reduced proprioceptive capabilities. All these factors tend to concentrate and accentuate the forces placed on the veneering porcelain.

Fracture of veneers is not a new problem. Traditionally, in ceramo-metal technology, the weakness of the veneering ceramic material has been compensated for by bulking up and designing the substructure in certain quite well defined ways. Nevertheless, bulking up the substructure often results in a less desirable aesthetic appearance, as the substructure becomes more visible through the veneer. One example of an attempt to provide a concealed support includes constructing a metal collar at the base of the substructure with a shoulder brought part way up the lingual surface of the substructure. Also, in the approximal regions the substructure frame is frequently built out under the contact points with the veneer. The concept behind these design elements is to reduce the bulk of the veneering porcelain and to convert the loading stresses on the veneer ceramic from being in shear to being under compression.

Many operators are applying the same concepts traditionally used for ceramo-metal technology to the design of high strength ceramic substructures. Notwithstanding, these design elements are not much help in strengthening the most visible portions of the teeth, the buccal surfaces. This can be a particular problem in the mandible because in a normally related occlusion, the buccal cusps of the mandibular teeth serve as occlusal supports. Using a high strength ceramic substructure, which tends to be opaque and of high luminosity, half way up the buccal surface to reinforce the veneer porcelain of the cusp is just as unacceptable as using a metal frame in the same manner. Furthermore, a marginal collar at the approximal regions of the substructure provides little or no reinforcement because it is so far away from the region where the stress is being applied (i.e. the tip of the buccal cusps).

Therefore, it would be beneficial to provide a strengthening mechanism for a crown and/or bridge close to the region where the stress is being applied to the veneer that does not compromise aesthetics and which is relatively simple to design and construct.

SUMMARY OF THE INVENTION

An object of the present invention is to provide a high strength substructure for prosthodontics, such as crowns and bridges. Another object of the present invention is to provide a process for manufacturing prosthodontics having a high strength substructure. Yet another object of the instant invention is to provide a substructure reinforcement for prosthodontic substructures. Still another object of the instant invention is to provide a process for manufacturing prosthodontics having a reinforced substructure. Another object of the instant invention is to provide a strengthening mechanism for prosthodontic substructures close to the region where the stress is being applied to the structure. Another object of the instant invention is to provide a prosthodontic substructure that is aesthetically pleasing and which is relatively simple to design and construct.

The objects of the instant invention are achieved through the use of an annular reinforcement structure generally running around the center of the crown of the piece. In a preferred embodiment of the instant invention, the substructure is made of a non-metal material. Instead of merely constructing a thin coping 20 over the foundation 10 (as is shown in FIG. 1), and instead of attempting to replicate the design structure used for a porcelain fused to metal restoration of the prior art, the reinforcement structure of the instant invention is designed at or about the height of contour of the crown. This is where the greatest thickness of veneering porcelain is usually located and lies right under where occlusal stresses will be applied.

In a preferred embodiment, the reinforcement structure of the instant invention is incorporated into the CAD-CAM design stage for a high-strength, milled substructure. The design of this reinforcement structure depends on the software associated with each CAD-CAM system. The reinforcement structure may be designed primarily manually using conventional CAD-CAM design software, which allows a user to place pre-made shapes down over an image on the screen, increase or decrease the existing shape, distort the shape in one/multiple vanishing points, increase the volume of the shape from a point-angle or free hand-paint an area. In one preferred embodiment, the reinforcement structure of the instant invention is designed primarily automatically by a CAD-CAM (or other software) application that includes a pull down annular shape that is placed around the concentric image being made over the die from a library of tools in the software palate. The annular shape may be enlarged (or reduced) in x, y, and z axis as necessary to bulk-up (or down) the core being designed. In another preferred embodiment, the reinforcement structure of the instant invention is designed primarily automatically by a CAD-CAM (or other software) application by the operator pulling the structure from a point, line, cluster of points, etc., to distort a portion of the shape of the main body of the substructure to create the reinforcement structure without distorting the overall shape of the main body. In yet another preferred embodiment, the reinforcement structure of the instant invention is pre-designed into the main body of the substructure. In such an embodiment, a basic shape for the main body of the substructure is selected from a library of shapes available in the software application based upon the desired shape for the final restoration, with the reinforcement structure already built into the shape of the main body. The operator then either pushes, pulls, takes away or otherwise erases portions of the pre-designed shape of the main body (including the reinforcement structure) to meet the needs for the specific restoration. In still another preferred embodiment, the substructure (including the reinforcement structure of the instant invention) is designed by first obtaining the desired shape for the restoration and then subtracting away or deconstructing from that shape to leave the substructure shape. In such an embodiment, the part of the final shape that is subtracted is determined to maximize the aesthetic appearance of the final restoration by concealing the substructure.

In one embodiment the reinforcement structure is over-built in the CAD-CAM design phase on a relatively freehand basis (or through use of the automatic software discussed above), preferably at the crest of the preparation, and protruding about 2 mm out from the base coping. After milling is completed, the contact regions are adjusted, and the amount of the lingual and labial prominence is modified as desired, by hand. If necessary or desired, the reinforcement structure is thinned out after milling. There is little requirement for bulk of the reinforcement structure because the high-strength non-metal substructure of the instant invention is not only strong, it is also very rigid. The final frame design is easy to design, construct and manage.

The aesthetic appearance of the piece is increased by reducing the potential for the sub-structure to "Shine-Through" the surface of the final restoration at the mesio-buccal region. To minimize Shine-Through, the prominent sub-structure may be reduced through the crown contour. Veneering porcelain is then applied over the deficiency. In addition, the reinforcement structure may be masked when the final restorations are characterized.

The reinforcement structure of the instant invention has the advantage that the marginal display of opaque porcelain from the underlying high strength core can be minimized, because there is no need for a heavy bulky collar to gain strength or to provide support. The normal thickness of the base coping can be extended to the margin. This is particularly useful in implant based units, where there tends to be a bigger build out from a relatively narrow base.

Although the scope of the instant invention is not limited to any specific materials for the substructures (or the veneers), it will be appreciated that the reinforcement structure of the instant invention is particularly well-suited for use with non-metal substructures. Due to the differential in thermal coefficients of expansion for most metal substructures from that of the overlying porcelain, a metal framework would tend to cool faster than the ceramic, possibly resulting in cracks in the veneer porcelain. In addition a more complex ceramic veneer construction may be needed to mask out a metal substructure than is necessary for a high strength ceramic framework.

The reinforcement support of the instant invention is remarkably simple to incorporate and use in practice. In one embodiment of the instant invention, for single unit restorations, a thin layer coping is designed over the preparation (such as a pre-manufactured implant abutment, a custom manufactured implant abutment, prepared portion of tooth on which restorations is supported, etc.) with a relatively crude shaping of the reinforcement structure. In the preferred embodiment, the inventive reinforcement structure is established at the height of the contact point and parallels the occlusal plane. When the reinforcement structure has been established relatively crudely in the design stage, it can then be refined quickly once the unit is positioned on a master model.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION OF A PREFERRED EMBODIMENT

As required, a detailed embodiment of the present invention is disclosed herein; however, it is to be understood that the disclosed embodiment is merely exemplary of the principles of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
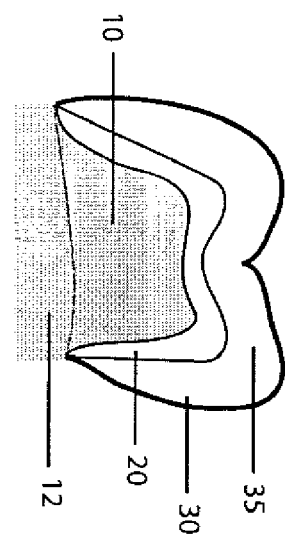
FIG. 1 is front elevation view of a dental implant including a conventional substructure.

Referring to FIG. 1, a dental implant including a conventional substructure is shown. As is shown in FIG. 1, the implant includes abutment portion 10 over which thin coping 20 is fit. Crown 30 is formed about coping 10 from a veneer porcelain to the shape of the final restoration. As can be seen in FIG. 1, a considerable amount of bulking out of the veneer porcelain is required to establish the final form of the restoration. The stresses from the mandibular posteriors tend radiate out from tip 35 of the buccal cusps. The conventional reinforcement structures, such as collar 12 located at the base of the substructure, are greatly limited in location due to aesthetic concerns. Because such reinforcement structures are located away from the region of stress, 35, fractures in the porcelain for crown 30 can occur.

Figure 2:
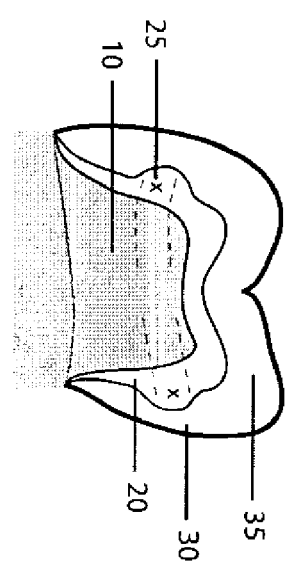
FIG. 2 is a front elevation view of a dental implant including an embodiment of the reinforced substructure of the instant invention.

Referring to FIG. 2, a dental implant including an embodiment of the reinforced substructure of the instant invention is shown. As is shown in FIG. 2, the implant includes abutment portion 10 over which coping 20 is fit. Coping 20 includes a body with a generally uniform outer surface and including annular protrusion 25 located generally near an occlusal portion of the restoration. As is done in the case of the prior art, crown 30 is formed about coping 20 from a veneer porcelain to the shape of the final restoration; however, crown 30 is also shaped around annular protrusion 25. As can be seen in FIG. 2, protrusion 25 is located near the location of the most considerable amount of bulking out of the veneer porcelain that is used to establish the final form of the restoration. As with the conventional restoration shown in FIG. 1, the stresses from the mandibular posteriors tend to radiate out from tip 35 of the buccal cusps; however, protrusion 25 is located in close proximity to (right under in the shown embodiment) this high stress region to provide a contact region and support for the veneering porcelain of crown 30. In addition to providing support, locating the relatively thin reinforcement 25 in the region of the thickest veneering porcelain also allows protrusion 25 to be concealed by the porcelain. In addition, the location of reinforcement protrusion 25 allows coping 20 to be relatively thin at the margin (base) resulting in optimal aesthetics for the restoration.

It will be appreciated that the use of the phrase "generally uniform" to describe the outer surface of the body of coping 20 of the instant invention refers to the fact that the outer surface of coping 20 generally (other than protrusion 25) does not include any significant variations in contour from those variations typically found in conventional coping structures which generally follow the contours of (i.e. are concentric with) the surface of the restorations for which they are substructures. Such contours often include various asymmetrical and irregular shapes that may include both concave and convex patterns in a single structure. Therefore, the generally uniform surface does not require the surface to be smooth or even, or of any standardized or symmetrical shape or form. It will further be appreciated that reference to the outer surface of the body of coping 20 as being generally uniform is not intended to require a uniform thickness for coping 20, even though the embodiment of coping 20 shown in FIG. 2 does include a generally uniform thickness.

As the shape of the outer surface of coping 20 will vary significantly, so to will the shape of protrusions 25. Although shown and described in the preferred embodiment as a generally annular, symmetrical shape (as protrusion 25), it will be appreciated that the contact region/support structure ("protrusion") of the instant invention may take on any number of shapes both symmetrical and asymmetrical, can be a single structure that generally encircles the substructure body (as is shown and described herein with respect to annular protrusion 25), can be multiple structures that generally encircle the substructure body, can be one or more substructures that partially encircle the substructure body, or can be one or more substructures that each protrudes from a single point along the substructure body. Furthermore, the terms "protrusion" and "protruding" are intended to include, but not be limited to, any convex shape that is not a coincident concentric duplicate shape of the preparation; any complex amplification of shape that is not just a convex derivative of the shape of the preparation; any shape having a concave approach from each side approach to an amplified area of protrusion that can not be described in simple harmonics, but only complex wave form; any superseding amplification of form that is not accidental or rendered for strictly artistic purpose; any concentric enlargement that is disproportionately distributed toward the superior (non-apical) portion of the long axis of the preparation; any asymmetrical appendage added to a design by computer generated pre-made shape or file added for specific structural considerations of subsequent materials added to a restoration infrastructure. Furthermore, it will be appreciated that the "protrusion" of the instant invention may be designed as an integral portion of an infrastructure (as is shown and described herein with respect to coping 20 protrusion 25), or alternatively, the "protrusion" may be a separate component that is attached to or otherwise combined with an infrastructure. Examples of "protrusion" shapes of the instant invention in addition to the generally annular protrusion 25 shown herein include but are not limited to bulges, power-swells, tumors, bumps, blobs, raised protuberances, etc.

As is shown in FIG. 1, conventional substructures tend to taper upward from the base of the substructure (located generally at the gums), so that the greatest thickness of veneering ceramic will be applied toward the top of the substructure, concealing the substructure at the location in which it would be most visible once finally installed. As is shown in FIG. 2, coping 20 of the instant invention also includes this upward tapering shape. Thus, as is already mentioned above, it will be appreciated that the phrase "generally uniform" with respect to the outer surface of coping 20 is not intended to limit the shape of the outer surface of coping 20, which can be generally cylindrical, conical, generally convex (especially for the majority of the labial and lingual portions) or any other simple or complex shape desired, whether now known or hereafter discovered.

In a preferred method of the instant invention, reinforcement protrusion 25 is incorporated into the CAD-CAM design stage for coping 20. In one embodiment coping 20 is milled from a ceramic material. Suitable materials for coping 20 include, but are not limited to, Lava™ two-stage zirconium dioxide system offered by 3M ESPE, and the Precident™ one-stage Bio-HIP Y-TZP (High Heat and Isostatic Pressure formed ytrium stabilized tetragonal zirconium polymorph) offered by DCS of Switzerland. The Lava™ System utilizes a zirconia dioxide block that is CNC milled in a greenware state then secondarily heat sintered. The Precident System mills directly from the harder presintered Bio-HIP Y-TZP block.

Coping 20, which includes protrusion 25, may be designed primarily manually using conventional CAD-CAM design software in which the user first designs coping 20 without protrusion 25 in the manner in which coping 20 of prior art substructures is design. The user then places pre-made shapes down over an image of coping 20 on the screen, increases or decreases the existing shape, distorts the shape in one/multiple vanishing points, increases the volume of the shape from a point or angle, or free hand-paints an area to add protrusion 25. In a preferred embodiment however, the coping 20 of the instant invention is designed primarily automatically by a CAD-CAM application that includes a pull down annular shape for protrusion 25 that is placed around the concentric image being made over the die for coping 20 which is chosen from a library of tools/shapes in the software palate. Protrusion 25 may be enlarged (or reduced) in x, y, and z axis as necessary to bulk-up (or down) the core being designed. In such an automated CAD-CAM application, the CAD-CAM software recognizes (or identifies) the outer contour shape (i.e. the surface) of coping 20 and conforms the inner surface of the pull-down annular shape for protrusion 25 to the outer surface of coping 20, such that the inner surface of protrusion 25 and the outer surface of coping 20 are aligned. If desired, the outer surface of protrusion 25 can also follow the shape of the outer contour of coping 20 by spacing each point of the outer surface of protrusion 25 an equal distance away from a corresponding point on the outer surface of coping 20.

In another preferred embodiment of the instant invention coping 20 of the instant invention is designed primarily automatically by a CAD-CAM application with the operator of the software pulling the structure from a point, line, cluster of points, etc., to distort a portion of the shape of the main body of the substructure without distorting the overall shape of the main body. Conventional modeling software primarily takes a shape and puts it in a "box" giving the operator the ability to pull at the corners to increase or decrease the volume of the shape or distort it. At all times, the operator is pulling the entire side of the 3D structure, not just the point. This is limiting as the software only allows symmetrical "pulls", and has a geocentric pivot point for the shape within the box. In this embodiment of the instant invention, the modeling software utilizes a geocentric pivot point that may be displaced anywhere within the volume and/or along any line or curved line of the CAD-CAM image of coping 20 so that the reinforcement structure of the instant invention (i.e. protrusion 25) may be "pulled" from the main body of the substructure (i.e. coping 20) without otherwise distorting the shape of the image of the body from which it is pulled.

Figure 3A:
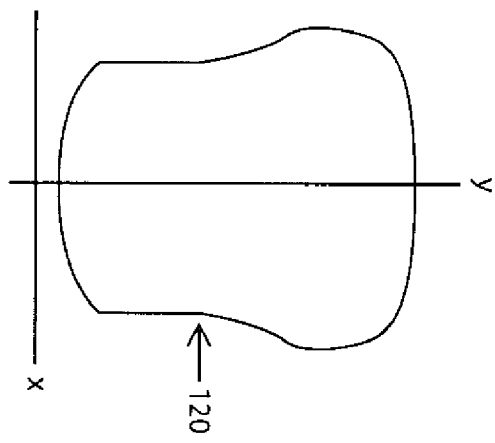
FIG. 3a is a front elevation view of a preliminary coping shape for use in an embodiment of the instant invention.
Figure 3B:
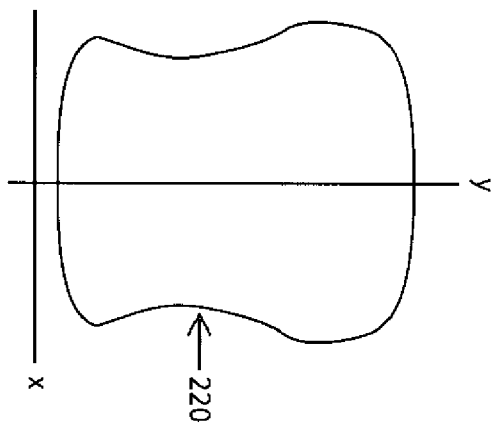
FIG. 3b is a front elevation view of an alternative embodiment of a preliminary coping shape for use in an embodiment of the instant invention.

In yet another preferred embodiment, the reinforcement structure of the instant invention is pre-designed into the main body of the substructure. In one such embodiment, a basic shape for the main body of the substructure is selected from a library of shapes available in the software application based upon the desired shape for the final restoration, with the reinforcement structure already built into the shape of the main body. Thus, the reinforcement structure shape is selected simultaneously with the main body shape. The operator then pushes, pulls, takes away or otherwise erases portions of the pre-designed shape of the main body and the reinforcement structure in the software to meet the needs for the specific restoration. FIGS. 3a and 3b show two alternative embodiments of shapes that can be used as preliminary or starting shapes in this particular embodiment of the instant invention. FIG. 3a shows a "door-knob" shape 120 that can be selected from a library in the design software; and FIG. 3b shows an alternative, "coke-bottle," shape 220. Once selected, the sides of preliminary coping shape 120 or 220 that is selected may be morphed, distorted or otherwise modified by pulling, pushing, taking away, erasing, etc., from the contact points. In a preferred embodiment, the sides are morphed by pulling from the contact points in pre-planned arcs of differing diameters, and controlled by looking down from the top of the shape (i.e. along the y-axis) to determine where (i.e. how many degrees around the outer surface of the shape) the selected morphing will occur. Examples of morphing include but are not limited to dragging the sides of the original shape apically or occlusally along the y-axis to make a symmetrical or asymmetrical (such as a French curve) arch, dragging the sides along the x-axis outwardly from the body of shape 120, and also along the z-axis. It will be appreciated that the blocks of material from which the substructure (such as coping 20) is milled may be pre-manufactured in shapes 120 and/or 220 to minimize the amount of waste material during the milling of the final substructure, once the substructure has been designed in accordance with the instant invention.

In still another preferred embodiment, the substructure (including the reinforcement structure of the instant invention) is designed by first obtaining the desired shape for the restoration and then subtracting away or deconstructing from that shape to leave the desired substructure shape. In such an embodiment, the part of the final shape of the restoration that is subtracted is determined to maximize the aesthetic appearance of the final restoration by concealing the substructure. In one such embodiment, the software constructs a "mesh framework of point clusters" that are external to (or in addition to) the point clusters established by the scan of the original piece that is being restored (or scan of a model of the piece to establish the desired external appearance of the restoration). These point clusters are used to construct an image of a "concentric" substructure (concentric to the original piece) for the restoration. The operator then embellishes or diminishes certain key areas, after rendering of the substructure image, to design the final substructure shape. Once the basic, overall shape has been rendered, the computer then knows in 3d, through the point clusters, where the operator is working, allowing the operator to easily take away portions of the image to result in a final image for the substructure.

Although shown and described in connection with a crown implant, it will be appreciated that the reinforcement structure of the instant invention can be used in connection with any dental restorations, including crowns and/or bridges, and including implant and/or restorations supported by teeth. Further, it will be appreciated that the materials used to manufacture the substructure (as well as the veneer) of the instant invention are not limited to those described herein. Although the inventive substructure is particular well suited for use with substructures manufactured of zirconium and other comparable ceramics, the inventive support structure may be utilized in connection with substructures manufactured from any other suitable material without departing from the spirit and scope of this instant invention.

It will also be appreciated that although the preferred method of the instant invention utilizes CAD-CAM design software, other methods of design (such as free-hand design, hologram or virtual reality modeling) now known or hereafter developed can be utilized without departing from the spirit and scope of the instant invention. Further, it will be appreciated that the inventive reinforcement may be used in connection any manufacturing process for crowns or bridges now known or hereafter discovered, including but not limited to simultaneous milling of a coping and implant abutment, milling the coping and abutment as a single piece, or milling of crowns and bridges from blocks or rods, etc. In addition, it will be appreciated that the infrastructures of the instant invention may be manufactured in methods other than the milling discussed herein. Alternative methods include but are not limited to press, lay-up, green ware production and subsequent milling or hand finishing.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations may be made in embodying the above invention, and in the construction thereof, other than those specifically set forth herein, may be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A dental restoration comprising:
   a one piece integrally formed substructure body having an open distal end, a closed proximal occlusal end and a side wall extending between said distal and proximal ends, said side wall including a generally uniform outer surface, said substructure body further including a support structure protruding from said outer surface of said side wall at a location spaced from, but generally near, said occlusal end of the substructure body, said support structure having a smooth shape and generally encircling the entire periphery of the substructure body, wherein the substructure body forms a hollow framework for receiving a dental preparation, and
   a veneer formed over and contacting the outer surface of the side wall, the support structure and the occlusal end of said substructure body;
   wherein said support structure is located generally proximate to the location of greatest occlusal stress and protrudes a distance from the surface of the side wall surface so as to provide support for said veneer that reduces the sheer stress exerted on said veneer.

2. The restoration as claimed in claim 1 wherein said support structure is generally annular.

3. The restoration as claimed in claim 1 wherein said support structure protrudes from said substructure body in a direction generally perpendicular to said surface.

4. The restoration as claimed in claim 1 wherein said support structure is made of a non-metal material.

5. The restoration as claimed in claim 1 wherein said substructure body comprises a coping adapted to be positioned over a preparation.

6. The restoration as claimed in claim 5 wherein said preparation is a tooth.

7. The restoration as claimed in claim 5 wherein said preparation is an abutment portion of an implant.

8. The restoration as claimed in claim 1 wherein said body comprises an abutment portion of an implant.

9. The restoration as claimed in claim 1 wherein said protruding support structure is generally tapered in shape from said substructure body to an outer end of said support structure.

10. The restoration as claimed in claim 9 wherein said support structure includes a generally curved surface.

11. The restoration as claimed in claim 10 wherein said outer end of said support structure includes a generally curved shape.

12. The restoration as claimed in claim 10 wherein said surface of said substructure body includes generally concave shapes along locations at which said support structure protrudes from said body.

13. The restoration as claimed in claim 1 wherein said support structure is generally located within a single plane.

14. The restoration as claimed in claim 13 wherein said support structure includes a generally curved surface.

15. The restoration as claimed in claim 1 wherein a shape of said substructure body is determined through the use of a software application.

16. The restoration as claimed in claim 15 wherein said software application is a CAD-CAM application.

17. The restoration as claimed in claim 15 wherein said software application determines a shape of said protruding support structure by identifying an outer contour shape for the substructure body, and conforming generally at least a portion of an annular protrusion shape to the outer contour shape.

18. The restoration as claimed in claim 17 wherein said identifying and conforming are accomplished generally automatically by a software application.

19. The restoration as claimed in claim 15 wherein said software application determines a shape of said protruding support structure simultaneously with determining a substructure body outer contour shape.

20. The restoration as claimed in claim 15 wherein said software application determines a shape of said substructure body by subtracting from a final desired shape for the restoration.

21. The restoration as claimed in claim 1 wherein said restoration is milled.

* * * * *